(12) United States Patent
Mirelman et al.

(10) Patent No.: US 6,689,588 B1
(45) Date of Patent: Feb. 10, 2004

(54) GARLIC ALLIINASE COVALENTLY BOUND TO CARRIER FOR CONTINUOUS PRODUCTION OF ALLICIAN

(75) Inventors: David Mirelman, Ramat Efal (IL); Meir Wilchek, Rehovot (IL); Talia Miron, Kfar Halm (IL); Aharon Rabinkov, Rehovot (IL); Hephzibah Sivaraman, Pune (IN)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/171,311

(22) PCT Filed: Apr. 14, 1997

(86) PCT No.: PCT/IL97/00124

§ 371 (c)(1),
(2), (4) Date: Sep. 12, 2000

(87) PCT Pub. No.: WO97/39115

PCT Pub. Date: Oct. 23, 1997

(30) Foreign Application Priority Data

Apr. 16, 1996 (IL) .................................. 117934

(51) Int. Cl.[7] .................. C12P 11/00; C12N 11/14; C12N 11/10; C12N 11/08; C12N 11/04
(52) U.S. Cl. .................. 435/130; 435/176; 435/177; 435/178; 435/179; 435/180; 435/182
(58) Field of Search ................. 435/174, 176, 435/177, 178, 179, 180, 182, 130

(56) References Cited

U.S. PATENT DOCUMENTS

| 5,244,794 A | 9/1993 | Prince et al. ................ 435/113 |
| 5,350,800 A | * 9/1994 | Verhoeven et al. ......... 525/54.2 |

FOREIGN PATENT DOCUMENTS

| DE | 40 12 884 A1 | 10/1991 |
| JP | 1289492 | 3/1988 |
| WO | WO 94/08614 | 4/1984 |

OTHER PUBLICATIONS

Chibata, Immobilized Enzymes, John Wiley & Sons N.Y., 1978, pp. 148–151.*
Thomas, et al., Biological Abstracts, vol. 92, 1991, Ref No., 51936.*
Appleton, J.A. and Tansey, M.R. (1975) Inhibition of Growth of zoopathogenic fungi by garlic extracts. *Mycologia 67:882–885.*
Augusti, K.T. and Mathew, P.T. (1974) Lipid lowering effect of allicin (diallyl disulphide oxide) on long term feeding to normal rats. *Experientia 30: 468–470.*
Barone, F.E. and Tansey M.R. (1977) Isolation, Purification, Identification, Synthesis, and Kinetics of Activity of the Anticandidal Component of *Allium Sativump*, and a Hypothesis for its mode of Action. *Mycologia 69: 793–825.*

Block, E. (1985) The chemistry of garlic and onions. *Sci. Am. 252: 94–99.*
Bordia, A., Arora, S.K., Kothari, L.K., Jain, K.C., Rathore, B.S. and Rathore, A.S. (1975) The Protective Action Of Essential Oils Of Onion And Garlic In Cholesterol–Fed Rabbits. *Atherosclerosis 22: 103–109.*
Bordia, A.K., Sanadhya, J.Y.K. and Bhu, N. (1977) Effect Of Essential Oil Of Garlic On Serum Fibrinolytic Activity In Patients With Coronary Artery Disease. *Atherosclerosis 28:155–159.*
Bordia, A. and Verma S.A. (1980) Effect Of Garlic Feeding On Regression Of Experimental Atherosclerosis In Rabbits. *Artery 7: 428–437.*
Cavallito, C.J. and Bailey, J.H. (1944) Allicin, The Antibacterial Principle Of Allium Sativum. I. Isolation, Physical Properties And Antibacterial Action. *J. Am. Soc. 66: 1944–1952.*
Cavallito, C.J., Buck, J.S. and Suter, C.M. (1944) Allicin, The Antibacterial Principle OfAllium Sativum. II. Determination Of The Chemical Structure. *J. Am. Chem. Soc. 66: 1952–1954.*
Friedmann, T.E. and Haugen, G.E. (1943) II. The Determination of Keto Acids In Blood and Urine. *J. Biol. Chem. 147: 415–442.*
Han, J., Lawson, L., Han, G. and Han, P. (1995) A Spectrophotometric Method For Quanitative Determination of Allicin and Total Garlic Thiosulfinates. *Anal Biochem. 225, 157–160.*
Jansen, H., Muller, B., and Knobloch, K. (1987) Allicin Characterization and its Determination by HPLC. *Plata Medica 53: 559–562.*
Kennedy, J.F. and Cabral, J.M.S. (1983) "Immobilzed Enzymes" *Solid Phase Biochemistry*, Scouten, W.H., ed., John Wiley & Sons, New York.
Kieswetter, H., Jung, F., Morwietz, C., Pindur, G., Heiden, M. and Wenzel, E. (1990) Effect of Garlic on Blood Fluidity and Fibrinolytic Activity: A Randomised placenbocontrolled double–blind study. *Brit. J. Clin. Pract. Suppl. 69:24–29.*
Knipschild, J.K. and Ter–Reit, G. (1989) Garlic, Onions and Cardiovascular Risk Factors. A review of the evidence from human experiments. Emphasis on Commercially available preparations. *Brit. J. Clin. Pharmacol. 28:535–544.*

(List continued on next page.)

Primary Examiner—David M. Naff
(74) Attorney, Agent, or Firm—Browdy and Neimark, P.L.L.C.

(57) ABSTRACT

Immobilized garlic alliinase wherein the alliinase is chemically, physically or biologically immobilized, is useful in a method for continuous production of allicin. The method comprises adding a solution of alliin as substrate to a column containing the immobilized garlic alliinase and collecting pure allicin in the effluent. The pure allicin is intended for use as food additive or for the preparation of pharmaceutical compositions for the treatment of viral, bacterial, fungal and parasitic infections, high levels of cholesterol and blood lipids, high blood pressure and thrombosis.

15 Claims, 4 Drawing Sheets

OTHER PUBLICATIONS

Kohn, J. and Wilchek, M. (1982) A New Approach (Cyano–Transfer) for cyanogen Bromide Activiation Of Sepharose At Neutral pH, Which Yields Activated Resins, Free of Interfering Nitrogen Derivatives, *Biochem. Biophys. Res. Commun. 107: 878–884.*

Lowry, O.H., Rosenbrough, N.J., Farr, A.L. and Randall, R.J. (1951) Protein Measurement with the Folin Phenol Reagent. *J. Biol. Chem 193: 265–275.*

Makheja, A.N. and Bailey, J.N. (1990) Antiplatelet Constituents of Garlic and Onion. *Agents Actions 29: 360–363.*

Mirelman, D., Monheit, D.J. and Varon, S. (1987) Inhibition of growth of enthamoeba histolitica by allicin, the active principle of garlic estract. *J. Infect. Dis. 156: 243–244.*

Miron, T. and Wilchek, M. (1982) A Spectrophotometric Assay for soluble and Immobilized N–Hydroxysuccinimide Esters, *Anal. Biochem. 126:433–435.*

Prabhune, A. and SivaRaman, H. (1990) Immobiliatin of Penicillin Acylase in Porous Beads of Polyacrylamide Gel. *Applied Biochem. and Biotech. 30:265–272.*

Rabinkov, A., Xiao–Zhu Z., Grafi G., Galili G. and Mirelman D. (1994) Allin Lyase (Alliinase) from Garlic (*Allium Sativum*). *Glycoconjugate J. 12: 690–698.*

Rabinkov, A., Wilchek M. and Mirelman D. (1995) Alliinase (alliin Lyase) from garlic (*allium sativum*) in glycosylated at ASN146 and forms a complex with a garlic mannose–specific lectin. *Glycoconjugate J. 12: 690–698.*

Stoll, A. Seebeck, E. (1949) Uberden enzymatischen Abbau des Alliins und die Eigenschaften der Alliinase. *Helv. Chim. Acta 32: 197–205.*

Stoll, A. and Seebeck, E. (1951) Chemical Investigations Of Alliin, The Specific Priniciple Of Garlic. *Adv. Enzymol. 11: 377–400.*

Tamper, J. (1983) "Organic synthesis using immobilized enzymes", in *Solid Phase Biochemistry*, Scouten, W.H., ed., John Wiley & Sons, New York.

Wilchek, M. and Miron, T. (1982) Immobilization Of Enzymes And Affinity Ligands Onto Agarose Via Stable and Uncharged Carbamate Linkages. *Biochem Int. 4: 629–635.*

Wilchek, M. and Miron, T. (1985) Activation of Sepharose with N,N–Disuccinimidyl Cabonate. *App. Biochem. Biotech. 11: 191–193.*

Thomas et al, "Immobilization and characterization of C–S lyase from onion (*Allium cepa*) bulbs", *Food Biotechnology*, 5(2):139–159 (1991).

* cited by examiner

GARLIC ALLIINASE COVALENTLY BOUND TO CARRIER FOR CONTINUOUS PRODUCTION OF ALLICIAN

FIELD OF THE INVENTION

The present invention relates to immobilized garlic alliinase in its biologically active form, and the use of said immobilized alliinase in a method for the manufacture of substantially purified allicin for use as active ingredient of pharmaceutical compositions and as food additive.

BACKGROUND OF THE INVENTION

Garlic and onions are members of the lilly family. Many medical properties have been ascribed to garlic and onions and they have been used in folk medicine for thousands of years.

A large spectrum of medical properties has been ascribed to garlic, *Allium sativum*, (Block, 1985). In moderm times the interest in the therapeutic properties of garlic has been resumed, and it is object of an increasing number of biochemical and clinical studies.

Garlic preparations are commercially available in the form of garlic oil, extracts, pills or tablets. Usually the preparation procedures of such garlic preparations are unknown, and the composition and amount of their active ingredients are not defined.

The active principles present in garlic have been found to be mainly sulfur-containing compounds. The principal component of a colorless oil obtained from steam distillates of garlic extracts was shown to be an unusual sulfur compound of formula $C_6H_{10}S_2O$, named allicin (thio-2-propene-1-sulfinic acid S-allyl ester) (Cavallito et al., 1944). Allicin was found to be a chemically unstable, colorless liquid that is thought to be responsible for both the odor and much of the biological activity of garlic.

Although allicin is responsible for the smell of garlic, a garlic bulb exhibits little or no odor until it is cut or crushed. The intact garlic clove does not contain allicin but rather its odorless precursor alliin (+)(S-allyl-L-cysteine sulfoxide) that is converted to allicin, pyruvate and ammonia by a C-S-lyase present in the garlic plant termed alliin lyase or alliinase [E.C. 4.4.1.4.] (Stoll and Seebeck, 1949). Alliin and alliinase are found in different compartments of the garlic clove. The cutting or crushing of the clove enables the enzyme to come into contact with the precursor of allicin.

Studies performed with garlic preparations confirmed some of the medical activities attributed to garlic. Thus garlic juice was shown to inhibit the growth of bacteria of the genera Staphylococcus, Streptococcus, Vibrio and Bacillus and of zoopathogenic fungi and many strains of yeast, including *Candida albicans* (Block, 1985; Appleton and Tansey, 1975; Barone and Tansey, 1977), and allicin was shown to exhibit antibacterial, antifungal and antiamebic activity (Cavallito et al., 1944; Barone and Tansey, 1977; Mirelman et al., 1987).

In the last few years, many studies reported the beneficial effects of garlic on cardiovascular risk factors, mainly hyperlipidemia and thrombogenesis in animals and in humans. The results of the administration of fresh garlic, etheric extracts, or its active component allicin were consistent: garlic induces an increase in fibrinolytic activity (Bordia et al., 1977; Kieswetter et al., 1990); inhibits platelet aggregation (Makheja and Bailey, 1990); and improves lipid profile including reduction of serum cholesterol levels (Bordia and Verma, 1980; Bordia et al., 1975; Knipschild and Ter-Riet, 1989; Augusti and Mathew, 1974).

These studies demonstrated a very impressive effect of garlic, but most studies were limited by several factors such as lack of controlled methods and suitable double-blind studies and use of preparations with unknown amount and chemical identification of the active ingredient.

Allicin was shown to exhibit the beneficial properties ascribed to garlic and thus it would be useful to produce allicin in controlled and known amounts for use as the active ingredient of pharmaceutical compositions. However, allicin is a very labile and volatile compound when exposed to air and the methods known today for its preparation are not satisfactory. The chemical synthesis involves many steps and is complicated, laborious, expensive, and very inefficient. The enzymatic method seems to be more attractive, however alliinase is a so-called "suicidal enzyme" that is rapidly and irreversibly inactivated by its own reaction product, allicin. Therefore a few minutes incubation of alliinase with the substrate alliin or its product, allicin, leads to a biologically inactive enzyme after one or a very limited number of cycles.

SUMMARY OF THE INVENTION

In order to overcome the above mentioned obstacles, the present invention provides alliinase in a form that is not inactivated by allicin. Thus, alliinase according to the invention can be used for the continuous preparation of allicin without losing its biological activity.

In one aspect, the present invention provides the garlic enzyme alliinase in an enzymatically active, immobilized form wherein the enzyme is chemically, physically or biologically immobilized on a support carrier.

Chemical immobilization according to the invention may be carried out by covalently binding the enzyme to a carrier selected from the group consisting of organic natural and synthetic polymers and inorganic carriers. Physical immobilization may be effected by entrapment of the enzyme within a polymer matrix or membrane, or its microencapsulation within semipermeable polymer membranes. Biological immobilization may be carried out by either binding biotinylated alliinase to an avidin-containing column or binding a cellulose binding domain (CBD) protein-modified alliinase to a cellulose column.

In another aspect, the invention provides a column comprising a chemically, physically or biologically immobilized garlic alliinase and a method for continuous production of substantially pure allicin using said column to which the substrate alliin is added.

By a further aspect, the present invention provides the use of substantially pure allicin produced according to the method of the invention for the preparation of pharmaceutical compositions for the treatment of viral, bacterial, fungal and parasitic infections, high levels of cholesterol and blood lipids, high blood pressure and thrombosis.

In yet another aspect the invention provides substantially pure allicin to be used as food additive or condiment.

Figure 1:
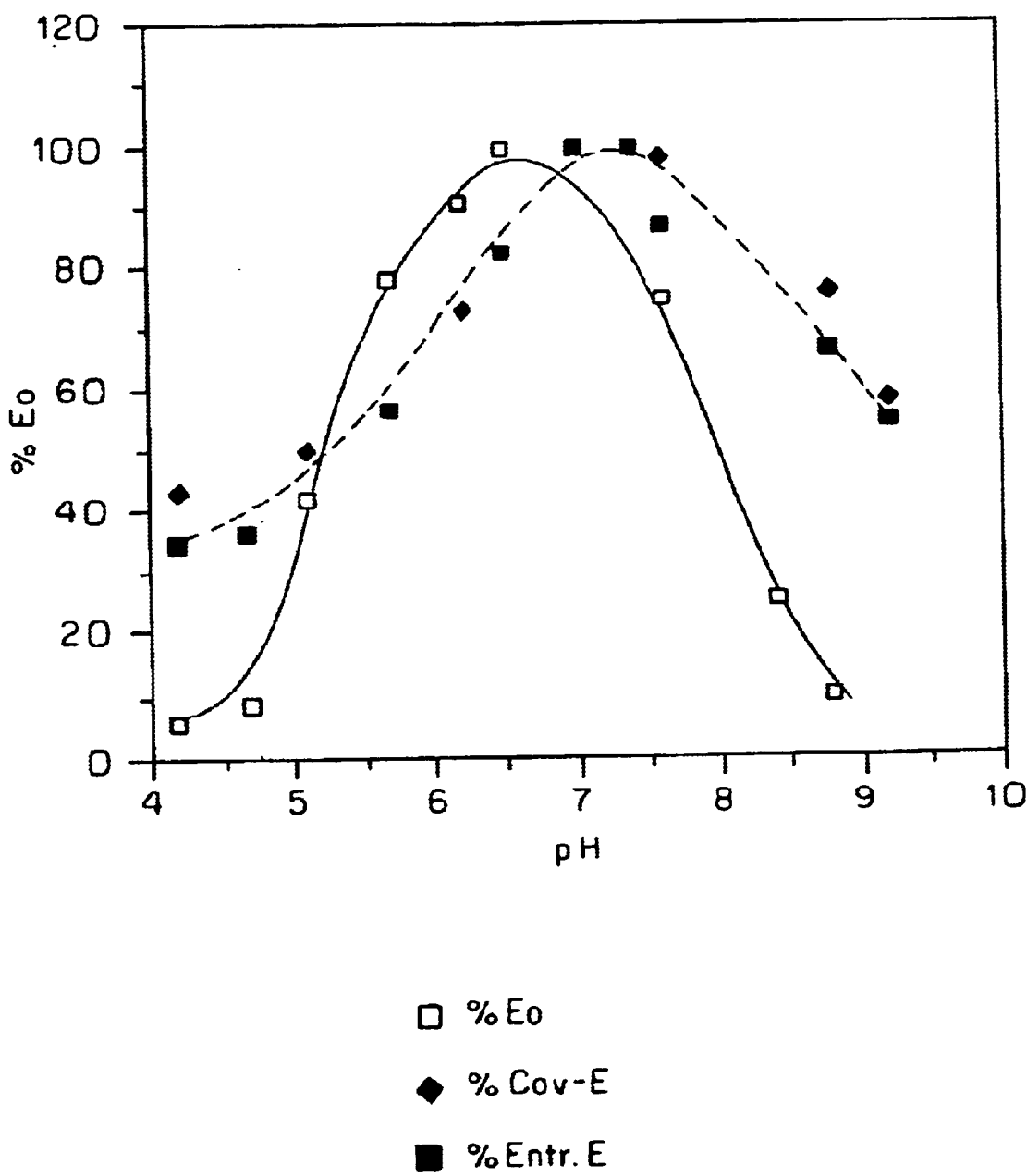
FIG. 1 shows the enzyme activity of soluble alliinase ($E_0$-dotted squares); alliinase covalently immobilized on Cl-Sepharose 4B (black losanges), and alliinase entrapped in agar/sodium alginate beads crosslinked with glutaraldehyde (black squares), as a function of pH.

1 (black squares), and entrapped alliinase as in FIG. 1 (black losanges), as a function of the assay temperature.

Figure 3:
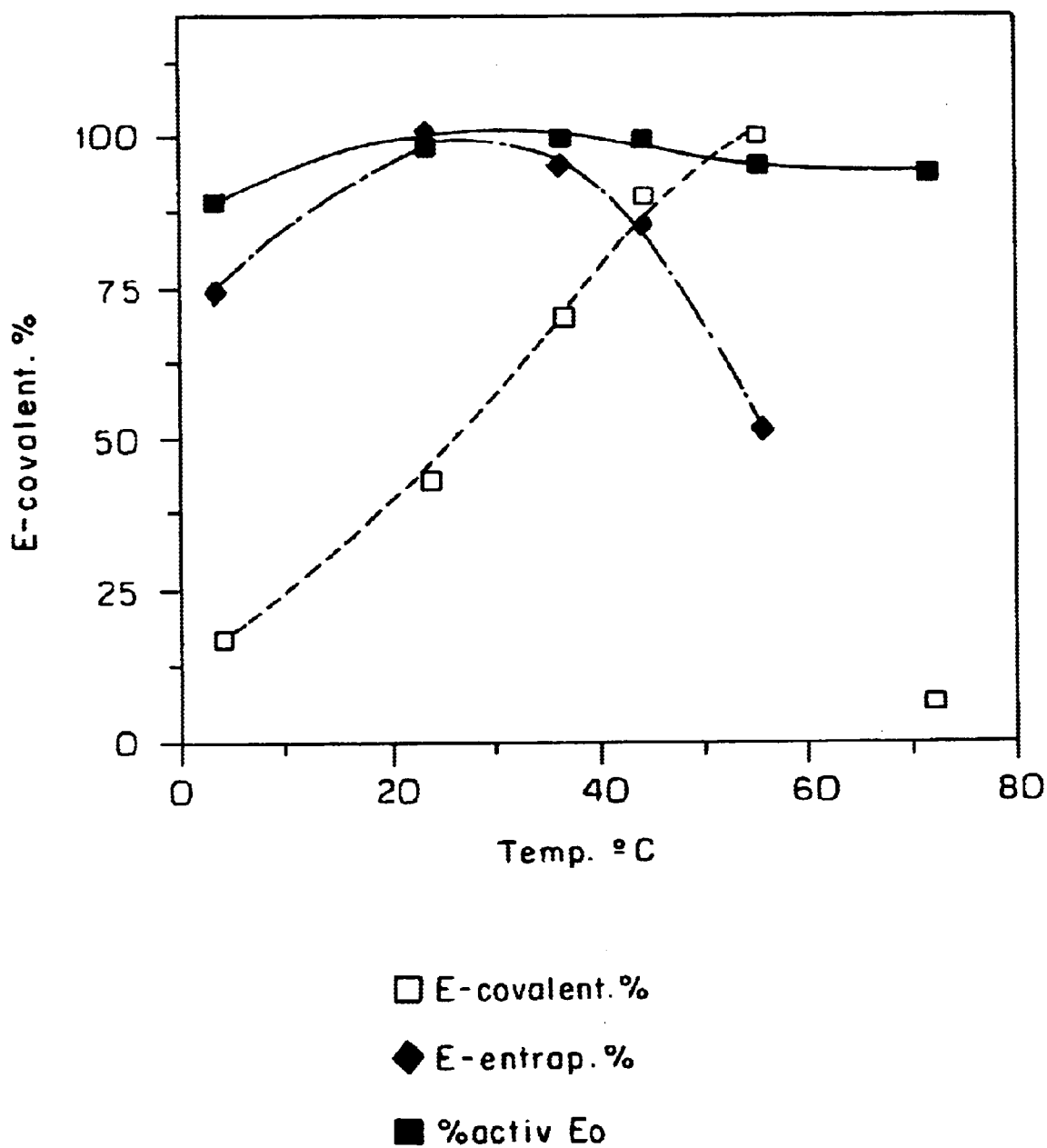

FIG. 3 shows enzyme activity of soluble alliinase ($E_0$-black squares); covalently immobilized alliinase as in FIG. 1 (dotted squares), and entrapped alliinase as in FIG. 1 (black losanges), as a function of pre-heating for 30 min at different temperatures before assay of the activity at room temperature.

Figure 4:
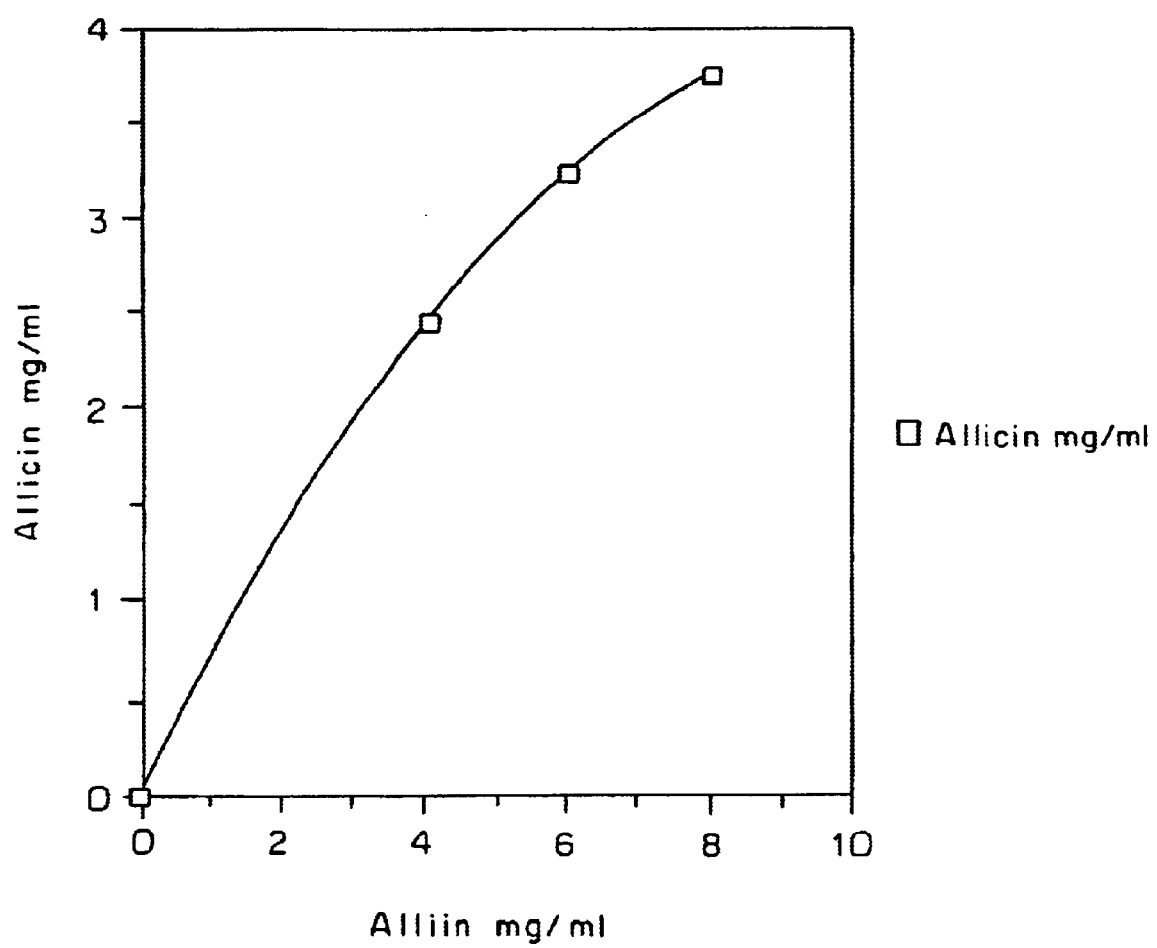

FIG. 4 shows the production of allicin (mg/ml) as a function of the amounts of alliin (mg/ml) added to a column of alliinase covalently bound as in FIG. 1.

DETAILED DESCRIPTION OF THE INVENTION

According to the present invention garlic alliinase is chemically, physically or biologically immobilized on a solid support. Any garlic alliinase, either natural or recombinant, may be used as long as the enzyme retains its catalytic activity.

Any suitable technique developed for immobilization of enzymes for biotechnological application, such as those described by Kennedy and Cabral, 1983, and Tramper, 1983, can be used according to the present invention.

Chemical immobilization may be carried out through covalent binding of the enzyme to a solid support by reaction between active groups of the support and one or more functional groups of the amino acid residues of the enzyme. Binding of the garlic alliinase to the carrier may be directly or via a spacer.

Any carrier suitable for the immobilization of enzymes such as the organic natural and synthetic polymers and the inorganic compounds described by Kennedy and Cabral, 1983, and Tramper, 1983, can be used according to the present invention.

Examples of inorganic carriers include, but are not limited to, controlled pore ceramics such as titania, zirconia, alumina, naturally-occurring porous minerals such as kieselguhr, attapulgite clays, pumice stone and bentonite, and controlled pore glass (CPG), a macroporous high-silica glass prepared from borosilicate glass.

Organic carriers used according to the invention include, but are not limited to, natural polymers such as polysaccharides, e.g. cellulose, starch, dextran, agar, agarose, chitin, chitosan, pectin, pectic acid, alginic acid and derivatives thereof; proteins, e.g. collagen and silk, and derivatives thereof; and synthetic polymers and derivatives thereof e.g. polystyrenes; polyacrylate-type polymers, e.g. polyacrylates, polymethacrylates, polymethacrylic acid anhydride, polyacrylamides, polyhydroxyalkyl methacrylates, polyglycidyl methacrylates, and polyacrylonitriles; maleic anhydride-based polymers, e.g. copolymers of maleic anhydride and ethylene; polypeptides, e.g. copolymers of L-leucine and 4-amino-DL-phenylalanine; vinyl and allyl polymers, e.g. chemically-modified polyvinylalcohol, polyallylalcohol, and vinyl ether copolymers; and polyamides, e.g. nylon. It is also encompassed by the invention to use a mixture of two or more of said carriers.

The coupling of enzyme molecules to solid supports involves mild reactions between amino acid residues of the enzyme and functional groups of the carrier. Some carriers possess such functional groups, e.g. maleic anhydride-based copolymers, methacrylic acid anhydride-based copolymers, nitrated fluoracryl methacrylic copolymers and iodoalkylmethacrylates. However, the support materials most commonly used do not contain these functional groups but rather hydroxy, amino, amido and carboxyl groups, which have to be activated for immobilization of the enzyme.

According to the mode of linkage, the method of covalent binding can be classified into diazo, peptide (amide) and alkylation methods, coupling by means of multifunctional reagents, and some miscellaneous procedures. Any of these methods can be used according to the invention, but one preferred embodiment relates to the peptide binding method. For this purpose supports containing carboxyl groups can be converted to reactive derivatives such as acyl azide, acid chloride, acid anhydride, isocyanate, imidocarbonate or cyclic carbonate, N-hydroxysuccinimide ester or p-nitrophenylester, and these derivatives form peptide bonds with free amino groups of the enzyme; or peptide bonds between free carboxyl or amino groups of the enzyme and, respectively, carboxyl or amino groups of the support, are formed using condensing agents such as carbodiimides and Woodward's reagent K.

According to the invention, a polysaccharide carrier such as cellulose or agarose (Sepharose™) is activated either by CNBr, forming a cyano ester or an imidocarbonate active group, or by N,N'-disuccinimidyl carbonate, or by a chloroformate derivative, e.g. p-nitrophenyl chloroformate or N-hydroxysuccinimidyl chloroformate, with formation of the corresponding carbonate active groups.

In another embodiment of the invention, a molecule serving as a spacer, such as an ω-aminocarboxylic acid, e.g. ε-amino-caproic acid, is first attached to the carrier through the $NH_2$ group and the free carboxyl group is activated to an active ester, e.g. N-hydroxysuccinimide ester, by reaction with suitable condensation reagents, e.g. carbodiimide and N-hydroxysuccinimide. Examples of such carriers include, but are not limited to, polysaccharides, e.g. cellulose and agarose (Sepharose™), and polyacrylates, e.g. Trisacryl™, a polymer of N-acryloyl-2-amino-2-hydroxymethyl-1,3-propanediol.

Physical immobilization of alliinase may be carried out by any standard procedure such as the methods described by Kennedy and Cabral, 1983 and by Tramper, 1983. It is based on the physical entrapment of the enzyme within a constraining structure, for example lattice of a polymer matrix or membrane, tight enough to prevent the release of the enzyme while allowing penetration of the substrate. Thus alliinase may be physically entrapped within a crosslinked water-insoluble polymer gel, such as polymer matrices made of naturally-occurring materials such as starch, collagen, gelatin, agar, calcium alginate and κ-carregeenan and crosslinked derivatives thereof, or crosslinked synthetic polymers such as polyacrylamides, poly(vinyl alcohol), poly (vinylpyrrolidone) and poly(meth)acrylates, e.g. poly(2-hydroxyethylmethacrylate). Methods for the preparation of entrapped enzymes include crosslinking of polymers by means of multivalent ions such as $Ca^{2+}$ and $Al^{3+}$, resulting in gelation of the enzyme-polymer solution, e.g. immobilization in calcium alginate gel; or polymerization or polycondensation of an aqueous solution of the monomers or oligomers, respectively, and the enzyme in the presence of a crosslinking agent, e.g. glutaraldehyde.

In another embodiment of the invention, alliinase may be physically-entrapped within microcavities of synthetic fibers, e.g. cellulose-based fibers such as cellulose acetate, or it may be microencapsulated within semipermeable polymer membranes, e.g. of nitrocellulose, nylon, polyurea or polystyrene, such that it cannot leak out while its substrate can diffuse across the membrane and be processed by the immobilized enzyme.

Biological immobilization of alliinase may be carried out, for example. using a cellulose-binding domain (CBD) protein coupled to alliinase followed by adsorption on cellulose, or by binding biotinylated alliinase to an avidin column, or by immobilizing haptenized alliinase onto a column of an antibody, e.g. antibody to dinitrophenol, fluorescein and the like. Examples of CBDs that can be used according to the invention include those described in published International PCT Patent Application No. WO 96/13524 co-owned by the applicants.

The invention further provides a column comprising an immobilized alliinase according to the invention and a method for the continuous production of substantially pure allicin that comprises adding a solution of alliin to such a column and collecting the allicin thus produced. Usually the allicin will be collected and stored in water solution at pH 4.5 (citrate buffer).

The substantially pure allicin may be used as food additive or condiment, for example to impart garlic flavour to oil, butter, cheese and the like, or as a natural food preservative in the meat or milk industry.

It may further be used for the manufacture of pharmaceutical compositions for human and veterinary use for treatment of several disorders including, but not being limited to, viral, bacterial, fungal and parasitic infections, high levels of cholesterol and blood lipids, high blood pressure and thrombosis. These pharmaceutical compositions are prepared by standard methods. In one embodiment, the allicin in citrate buffer pH 4.5 may be stored in airless sealed capsules.

The pharmaceutical compositions of the invention can be used for the treatment of bacterial infections caused by bacteria of the genera Staphylococcus, Streptococcus, Vibrio and Bacillus, of fungal infections caused for example by *Candida albicans*, as antiamebic and in the treatment of heart diseases and artheriosclerosis.

The invention further provides a shunt consisting of a column comprising immobilized alliinase for treatment of thrombosis, and the ex vivo use of such a column for treatment of thrombosis and for hemodialysis and peritoneal dialysis. In the peritoneal dialysis, for preventive antibacterial treatment, alliin is added to a tube containing the immobilized alliinase that is placed after the dialisys system.

The invention will now be illustrated by the following non-limiting examples.

EXAMPLES

Materials and Methods

In the examples, the following materials and methods will be used.
(i) Materials
Garlic was obtained from local market; crosslinked agarose (Cl-Sepharose™ 4B) was from Pharmacia; agar, alginic acid (sodium salt), beaded cellulose (50–80 mm), 2,4 dinitrophenylhydrazine, 5,5' dithiobis-(2-nitrobenzoic acid) (DTNB), and glutaraldehyde were all from Sigma; Trisacryl GF2000 (LKB); p-nitrophenyl chloroformate, 4-(dimethylamino)-pyridine (DMAP), N,N,N',N'-tetramethyl (succinimido)uronium tetrafluoroborate (TSTU), and 6-aminocaproic acid were obtained from Fluka (Buchs, Switzerland);
(ii) Synthesis of Alliin
Alliin was synthesized from L-cysteine and allyl bromide following oxidation by $H_2O_2$ by the procedure of Stoll and Seebeck, 1951. The stereospecific product obtained, (+)S-allyl-L-cysteine sulfoxide (M.P.=164°, $[\alpha]_D$ in $H_2O$+62.1°), was identical to the natural substrate, alliin (Yield: 15.7%).
(iii) Preparation of Garlic Alliinase
Alliinase was isolated from garlic cloves as previously described (Rabinkov et al., 1995). In short, 100 gr of peeled garlic cloves were minced and extracted with 150 ml of extraction buffer [Na-phosphate buffer 0.02M pH 7.4, containing glycerol 10%, pyridoxal-5'-phosphate 0.02 mM], and magnetically stirred for 30–45 min at 4° C. The supernatant was collected by centrifugation and fractionated by one of the following procedures: (i) acetone precipitation by adding 0.65 volume of cold acetone and collecting the pellet by centrifugation; (ii) precipitation with ammonium sulfate at 50% saturation and collecting the pellet by centrifugation; or (iii) precipitation with polyethyleneglycol-8000 [PEG 8000] at 25% final concentration and collecting the pellet by centrifugation. Before the PEG precipitation, a pre-run on immobilized iminodiacetic acid (IDA) column, equilibrated with nickel, was sometimes carried out. The pellet in all cases was dissolved with 50 ml of extraction buffer and was either dialyzed or gel-filtered through Sephadex G-25 (250 ml column). Further purification was done by chromatography through hydroxylapatite column (Ceramic HAP, Bio-Rad). After washing of the column with 0.05 M phosphate buffer, the alliinase peak was eluted with 0.2 M Na-phosphate buffer and was directly used for immobilization.
(iv) Protein was Determined According to Lowry et al., 1951.
(v) Alliinase Activity:
  a) Direct Assay
  (1) Enzymatic assay by measuring pyruvic acid formed as a byproduct of the alliinase reaction with alliin, as described by Rabinkov et al., 1994.The standard reaction mixture contained Na-phosphate buffer (0.1M, pH 6.5), pyridoxal 5'-phosphate (0.025 mM), NADH (0.2 mM), lactic dehydrogenase (10 U), alliin (6 mM). and an alliinase sample in a total vol of 1 mL. Enzymatic activity was monitored spectrophotometrically by the decrease in absorbance at 340 nm using cuvets of 1 cm path length. A unit of activity was defined as the amount of enzyme required to release 1 $\mu$mol of pyruvate per min.
  (2) Spectrophotometrically measuring at 520 nm the product obtained upon reaction of pyruvic acid with dinitrophenylhydrazine as previously described (Friedemann and Haugen, 1943).
  (3) Measurement of allicin by HPLC (Rabinkov et al. 1994)
  b) Indirec Assay:
  Spectrophotometric determination of allicin by reaction of allicin with excess cysteine and measuring the remaining cysteine by reaction with DTNB as previously described (Han et al., 1995).
(vi) Allicin Analysis
The procedure for the isolation of allicin as a standard was carried out according to Jansen et al., 1987. Alliin (300 mg) was dissolved in 300 ml of 0.1 M Na-phosphate buffer, pH 6.5, and incubated at 37° C. together with purified alliinase (30 units/mg). After 2 h of incubation the solution was extracted twice with ether and dried over $Na_2SO_4$. Ether was removed with a stream of dry air at room temperature. Allicin (92 mg) was dried in a refrigerated dessicator over sulfuric acid (98%).
(vii) Thin Laver Chromatography (TLC)
TLC identification of S-allyl-L-cysteine and alliin was carried out on precoated cellulose plates (Merck, Darmstadt, Germany) using as solvent n-butanol-acetic acid-$H_2O$ (4:1:1 v/v/v). After drying, the plates were sprayed with ninhydrin (0.25%) reagent and placed in an oven at 110° C. for 10 min. Allicin ($R_f$=0.375) was identified by chromatography on silica gel plates (Merck) using a solvent system consisting of benzene-ethyl acetate (90:10), and detected on the plates by free iodine vapour.

(viii) Quantitative Determination of Alliin and Allicin

Quantitative determinations of alliin and allicin were obtained using an LKB HPLC system with an SP 4290 integrator (Spectraphysics). The separation was achieved on a LiChrosorb RP-18 column using as eluant methanol (60%) in water containing 0.1 % formic acid. Alliin emerges after about 4.5 min and allicin after about 9 min.

Example 1

Preparation of Covalently Immobilized Alliinase (a) Cellulose, Trisacryl™ and Sepharose™ containing the spacer ε-amino caproic acid were prepared according to Wilchek and Miron (1982), and converted to the N-hydroxysuccinimide esters using N,N,N',N'-tetramethyl (succinimido) uronium tetrafluoroborate (TSTU) or carbodiimide and hydroxysuccinimide. Quantitation of the active groups was done according to Miron and Wilchek (1982).

In a typical procedure, 10 g of activated gel containing the N-hydroxysuccinimide active group were washed on sintered glass funnel with cold water for a few minutes and resuspended in 10–40 ml of alliinase solution (2–5 mg/ml) in phosphate buffer 0.02M pH 7.4. The suspension was shaked 4–16 hours at 4° C.

(b) Sepharose or beaded cellulose were activated either by the CNBr method according to Kohn and Wilchek (1982), or by using N,N'-disuccinimidyl carbonate (DSC) according to Wilchek and Miron (1985), or p-nitrophenyl chloroformate or N-hydroxysuccinimide chloroformate according to Wilchek and Miron (1982). Quantitation of the active groups was done according to Miron and Wilchek (1982). These activated carriers were used for direct coupling of alliinase without spacer.

For the covalent coupling of alliinase to CNBr- or p-nitrophenylcarbonate-activated gel, e.g. Sepharose™, the coupling mixture was adjusted to 0.2M $NaHCO_3$ final concentration, and the coupling time was at least 16 hours at 4° C. Conjugates were filtered and the amount and activity of unbound protein was determined. The gels were washed with 0.1M ammonia followed by phosphate buffer pH 7.4 (0.05M).

Example 2

Preparation of Entrapped Alliinase

Entrapment of alliinase in agar beads was done according to Prabhune and SivaRaman, (1990). Agar (2.0 g) and sodium alginate (0.5 g) were suspended in water (50 ml) and dissolved by heating in boiling water bath. The suspension was cooled to 50° C. and alliinase (50 ml) was added upon stirring to form a homogeneous suspension. The suspension was dropwise added via peristaltic pump into calcium chloride (2%; 500 ml) containing glutaraldehyde (1%). Stirring continued in calcium chloride/glutaraldehyde for 1 hour. Removal of calcium alginate was done by washing the beads with sodium phosphate buffer, pH 7.4 (0.05 M), till the washings were clear. The beads were further washed with water and stored at 4° C.

Example 3

Analysis of Immobilized Alliinase

Determination of bound protein to carrier in the immobilized alliinase preparations of Examples 1 and 2, was done by substraction of the amount of unbound protein in the coupling solution from the amount taken for the coupling.

Assay of immobilized alliinase activity was done in a batchwise mode: 50 μl of alliin [100 mg/ml buffer assay] was added to an aliquot of suspension of an immobilized alliinase 50 mg wet gel/ml buffer phosphate 0.05M pH 6.5 containing 0.2 mM pyridoxal-5'-phosphate [assay buffer] in Eppendorf tube (final volume 1.0 ml). The reaction procceeded for 3–5 min while shaking, and the supernatant was collected either by centrifugation or by filtration. 50 μl samples of the supernatant were taken for determination of pyruvic acid or allicin concentration.

Assay of soluble enzyme activity was done in a similar way. Reaction was stopped by adding trichloroacetic acid (TCA) to a final concentration of 5%.

For the assay of pyruvic acid, to an aliquot of 50 μl of the enzymatic reaction, were added 50 μl of 10% TCA (in case of immobilized alliinase) or 50 μl of 5% TCA (in case of soluble alliinase), and 50 μl of 0.1% 2,4 dinitrophenylhydrazine in 7% HCl, mixed and kept for 5 min at room temperature. Then 0.25 ml of toluene (water saturated) was added and the mixture was vortexed for 30", and kept 5 min at room temperature. An aliquot of the organic phase (25–50 μl), was added to 0.55 ml of 2.5% KOH in ethanolic solution, kept 10 min at room temperature and absorbance measured at 520 nm. Calibration was done with 10 mM pyruvic acid (10–30 μl) samples.

For the allicin indirect assay, to an aliquot of 50 μl of the enzymatic reaction, was added 150 μl of fresh solution of cysteine (0.02M) in HEPES buffer pH 7.4 (50–500 mM). After 10 min at room temperature, 5 μl aliquot was diluted with DTNB (0.2 mg/ml in 50 mM HEPES pH 7.4), and absorbance was read at 412 nm ($E_M$ 412 13600). The concentration of reacted cysteine with allicin was calculated by substraction of the observed A412 (non reacted cysteine) from A412 of cysteine without enzyme (cysteine=100%).

Unit activity: calculated as μmole pyruvic acid $min^{-1}$.
Specific activity: μmole pyruvic acid $min^{-1}$ $mg^{-1}$.

For the allicin direct method, allicin concentration in effluent was assayed by directly applying 50–100 μl of the diluted sample (diluted 1:100 with running buffer) onto an RP C-18 HPLC column. Allicin and alliin retention times were about 8.5 min and 4.5 min, respectively.

3(i). Specific Activity of Soluble and Immobilized Alliinase and Amount of Aliinase Coupled to Insoluble Carrier The specific activity of the various purified alliinase preparations (method iii) and of alliinase immobilized on Cl-Sepharose are shown in Table 1. The different specific activities indicate the extent to which the enzyme was purified. Interestingly in some cases the immobilized alliinase showed higher specific activity than the soluble enzyme, probably because the soluble enzyme is unstable upon storage.

TABLE 1

Specific activity of soluble and immobilized alliinase and the amount of protein bound

| Preparation method | Protein mg/100 g garlic | Specific activ. of soluble alliinase* | Protein bound mg/wet weight g-Cl-Sepharose | Specific activ. of alliinase immobilized on Cl-Sepharose** |
|---|---|---|---|---|
| a. Acetone ppt. | 120 | 11.1 | 2 | 9.6 |
| b. Amm. sulph. ppt. | 422 | 5.7 | 8.3 | 4 |
| c.1 PEG8000 ppt. | 90 | 66.5 | 2.2 | 96 |
| c.2 IDA/PEG ppt. | 63 | 73.4 | 1.8 | 195 |

*Specific activity of soluble enzyme: $\mu$mole pyruvate.min$^{-1}$.mg$^{-1}$
**Specific activity of bound enzyme: $\mu$mole pyruvate.min$^{-1}$ mg enzyme bound$^{-1}$.

It seems that the specific activity of immobilized enzyme depends on the method by which the enzyme was prepared and on the specific activity of the soluble enzyme. The higher the specific activity of the soluble enzyme, the higher is the specific activity of the immobilized enzyme. It is clear that there is no loss of activity due to immobilization.

Interestingly, there is not much difference with the carrier being used and the method of its activation. Of course preference should be given to methods which result in stable bonds, e.g. amides, urethanes (carbamates), with minimal leakage of protein. In this particular case, the activation with DSC gives the most stable derivatives of alliinase with the highest specific activity as shown in Tables 2 and 3.

TABLE 2

Specific activity and amount of protein bound of alliinase immobilized in different ways

| | Cellulose-6-amino caproyl | Sepharose-6 amino caproyl | Trisacryl-6-amino caproyl | Sepharose (CNBr) | Sepharose (DSC) | Agar/entrapped |
|---|---|---|---|---|---|---|
| Protein bound mg/g wet gel | 21.7 | 5.6 | 3.2 | 5.3 | 2.6 & 8.3* | 1.9 |
| Specific activity** | 8.5 | 4.2 | 5 | 9.6 | 195 & 6.9* | 2.9 |

*different experiment (different enzyme prep)
**Specific activity: $\mu$mole pyruvate.min$^{-1}$.mg protein bound$^{-1}$

TABLE 3

Specific activity of soluble alliinase and of alliinase immobilized in different ways

| Date of prep. | Specific activity of soluble alliinase | Carrier | Specific activity of immobilized alliinase |
|---|---|---|---|
| 4.7.95 | 8.4 | Cl-Sepharose-6-aminocaproyl | 4.2 |
| — | 8.4 | Agar entrapment | 2.9 |
| 25.10.95 | 11.2 | Cl-Sepharose 4B | 9.4 |
| | 11.2 | Cl-Sepharose 6-amino caproyl | 13 |
| | 11.2 | Trisacryl GF2000-6-amino caproyl | 5.0 |

TABLE 3-continued

Specific activity of soluble alliinase and of alliinase immobilized in different ways

| Date of prep. | Specific activity of soluble alliinase | Carrier | Specific activity of immobilized alliinase |
|---|---|---|---|
| 13.11.95 | 66.5* | Cl-Sepharose 4B | 96 |
| | 73.4* | Cl-Sepharose 4B | 195 |

*assay of soluble enzyme prep. was done after 1 day at cold room

3(ii). Effect of pH on Enzymatic Activity of Alliinase

To study the enzymatic activity of soluble alliinase prepared by acetone precipitation, Cl-Sepharose 6-aminocaproyl-covalently immobilized alliinase and entrapped alliinase in agar beads as a function of the pH, samples of immobilized enzyme either covalently bound or entrapped as well as soluble enzyme prepared by acetone precipitation were incubated at room temperature in buffers (0.05 M) over a pH range of 4–9.5 for a period of 5 min in presence of alliin. The reaction mixture contained the enzyme, LDH 2.5–5.0 U/ml, NADH 0.2 mg/ml (0.26 mmole/ml). Reaction started by adding the substrate alliin from a concentrated solution (100 mg/ml) to final concentration of 2 mg/ml alliin. Reaction was run at room temperature for 5 minutes. The activity, measured as decreasing absorbance at 340 nm, was recorded directly for the soluble enzyme; for the immobilized (0.5–1.0 mg conjugate per ml) and the entrapped enzyme (1 bead per ml), it was measured after shaking the reaction mixture 5–15 minutes, followed by centrifugation. Enzymatic reaction was estimated as the decrease of optical density at 340 nm per minute. The highest activity was considered as 100%.

As shown in FIG. 1, the soluble alliinase(dotted squares) as well as the entrapped alliinase (black squares) showed a bell type shaped graph with optimum pH assay at 6.5–7.0, while the covalently bound alliinase (black losanges) showed optimum activity at pH 7.0–7.5. Due to the increased stability of the product allicin at acidic pH it was decided to continue the reaction with immobilized enzyme at pH 6.5.

3(iii). Effect of Temperature on the Enzymatic Activity of Alliinase

The enzymatic activities of alliinase (1–2 µl of dissolved pellet after crude acetone preparation), Cl-Sepharose-covalently immobilized alliinase (1 µg gel) and agar entrapped alliinase (1 bead about 40 mg gel) were studied as a function of the assay temperature. Samples of suspension of Cl-Sepharose immobilized enzyme as well as aliquots of soluble enzyme were incubated with alliin (2–5 mg/ml) in 0.1 M phosphate buffer containing 0.2 mM pyridoxal-5-phosphate pH 6.5 (0.85 ml) for 5 min at different temperatures. Reaction was stopped by adding 0.1 ml 50% TCA. The carriers Cl-Sepharose-conjugate as well as agar-entrapped-alliinase were removed by centrifugation and pyruvic acid concentration was determined in the supernatant with 2,4-dinitro-phenylhydrazine according to Friedmann and Haugen (1943). The highest activity of each preparation was considered as 100%.

Figure 2:
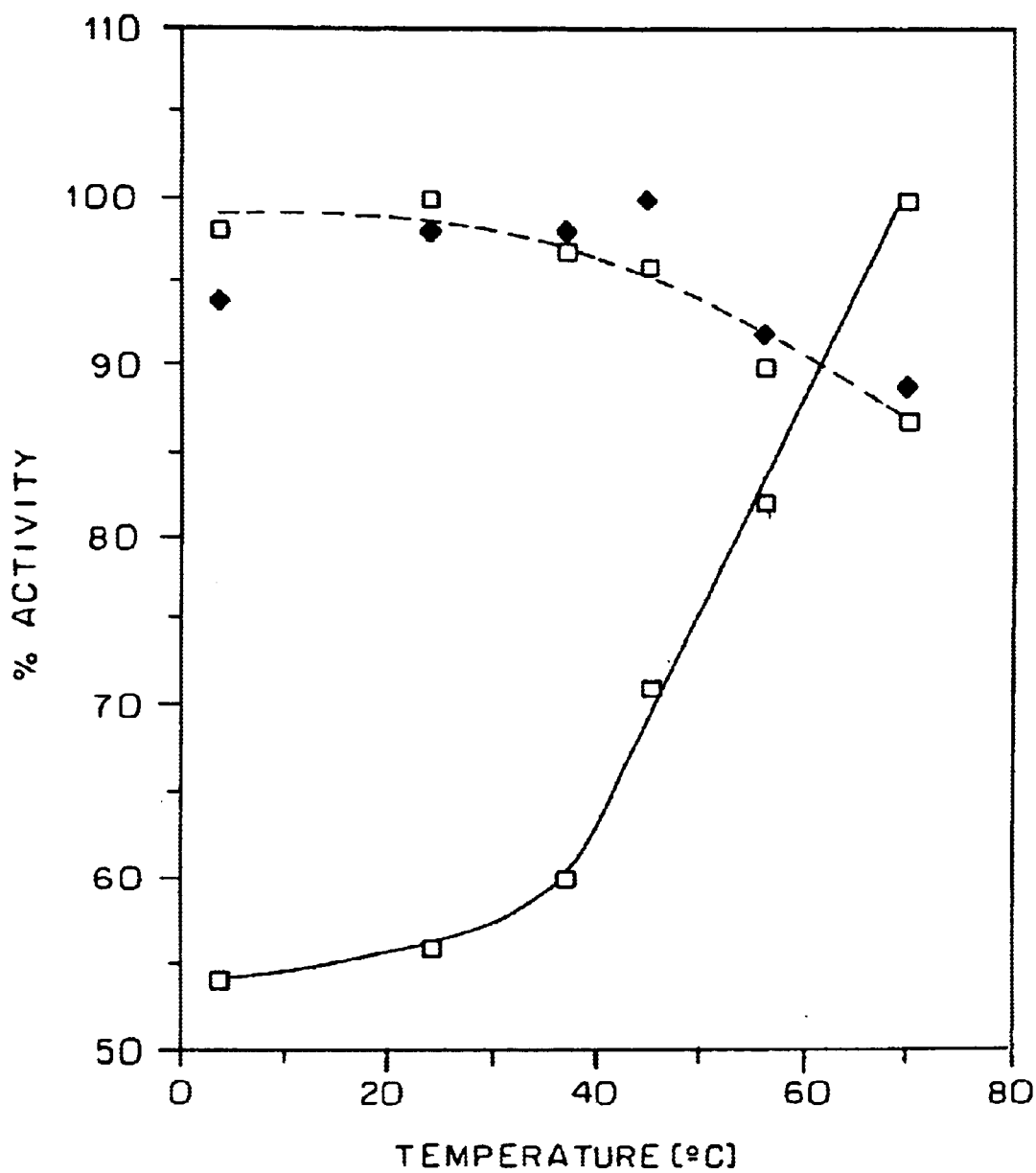
FIG. 2 shows enzyme activity of soluble alliinase ($E_0$-dotted squares); covalently immobilized alliinase as in FIG.

As shown in FIG. 2, there was no significant difference in the activities of the soluble enzyme (dotted squares) or the entrapped enzyme (black losanges) in the range of temperature measured (+/-10%). The covalently bound enzyme (black squares) was found to be much more active at temperatures above 40° C. The activity at room temperature was found to be about 50% of that observed at 70° C. In view of the fact that the reaction goes to completion also at room temperature, most of the work was performed at room temperature.

3(iv). Effect of Temperature on the Stability of Alliinase

Assay of enzyme activity at pH 6.5 room temperature, was done after preincubation of the enzyme preparations (soluble alliinase, Cl-Sepharose-conjugate of alliinase and entrapped alliinase) at different temperatures, in assay buffer pH 6.5 for 30 minutes. The residual enzyme activity was determined after incubation with alliin for 5 min. The enzymatic reaction was stopped by TCA, and the amount of pyruvate was assayed.

The results are shown in FIG. 3, wherein soluble alliinase (prepared by acetone precipitation pellet dissolved to 3.86 mg protein/ ml) 2 µl/ml (dotted squares); covalently bound Cl-Sepharose-6-aminocaproyl alliinase (soluble enzyme prepared by acetone precipitation: 5–6 mg /g gel) 1 mg gel/ml (black squares); entrapped alliinase (prepared by acetone precipitation and entrapped as described in Example 2), 1 bead/ml (40 mg gel) (black losanges).The highest activity of each preparation was considered as 100%. As shown in FIG. 3, no loss of activity was found for the native enzyme. The entrapped enzyme showed no change in activity at temperatures between 25–56° C., but lost about 50% of its activity after preheating at 72° C. The activity of the covalently bound enzyme increased upon preheating at temperatures between 25–56° C., but preheating at 72° C. resulted in loss of 50% of its activity at room temperature.

Example 4

Continuous Production of Allicin on a Column of Immobilized Alliinase

The immobilized alliinase with different specific activities were packed in columns of different sizes and alliin solution at different concentrations (up to 10 mg/ml) in buffer phosphate 50 mM, containing pyridoxal-5-phosphate 0.2 mM, pH 6.5, was added at a loading rate of 7 ml/h at room temperature. For immobilized enzyme with low specific activity, e.g. 1–2 U $min^{-1}ml^{-1}$, larger column (1×10 cm) were used, while for immobilized enzyme with high specific activity, e.g. ~100 µmole pyruvic acid $min^{-1}m^{-1}$, smaller columns (1×7 cm) were used. Flow rate of column was 7 ml/h at room temperature. Efficiency of allicin production was proportional to the specific activity of the immobilized alliinase. Columns containing only 1–2 units activity/ml carrier (1×10) already converted continuously 70–82% of alliin solution (5 mg/ml) to allicin.

In a particular example, alliinase covalently immobilized onto Cl-Sepharose was packed in a column (1.5×7 cm). Alliin was loaded at different concentrations (up to 10 mg/ml) in buffer phosphate 50 mM, containing pyridoxal-5'-phosphate 0.2 mM, pH 6.5, at a loading rate of 7 ml/h at room temperature. The concentration of allicin in the eluate was determined. As shown in FIG. 4, the efficiency of this column containing high specific activity immobilized enzyme showed almost linear dependence on the concentration of the substrate alliin.

Example 5

Long-term Stability of Immobilized Alliinase

Immobilized Cl-Sepharose-6-aminocaproyl alliinase packed in a 1.5×7 cm column was used for continuous production of allicin for two weeks at room temperature under loading conditions of 7 ml/h of alliin 5 mg/ml in 50 mM buffer phosphate containing 0.2 mM pyridoxal-5'-phosphate, pH 6.5. The column showed no loss of activity over this period of use. Storage of the column at 4° C. for a period of 2 months, did not change the efficiency of the immobilized alliinase and could be used for further production of allicin.

REFERENCES

1. Appleton, J. A. and Tansey, M. R. (1975) Inhibition of growth of zoopathogenic fungi by garlic extracts. Mycologia 67: 882–885.
2. Augusti, K. T. and Mathew, P. T. (1974) Lipid lowering effect of allicin (diallyl disulphide oxide) on long term feeding to normal rats. Experientia 30: 468–470.
3. Barone, F. E. and Tansey, M. R. (1977) Isolation, Purification, Identification, Synthesis, and Kinetics of Activity of the Anticandidal Component of *Allium Sativum*, and a Hypothesis for its mode of action: Mycologia 69: 793–825.
4. Block, E. (1985) The chemistry of garlic and anion. Sci. Am. 252: 94–99.
5. Bordia, A., Arora, S. K., Kothari, L. K., Jain, K. C., Rathore, B. S. and Rathore, A. S. (1975) The protective action of essential oils of onion and garlic in cholesterol-fed rabbits. Atherosclerosis 22: 103–109.

6. Bordia, A. K., Sanadhya, J. Y. K. and Bhu. N. (1977) Effect of essential oil of garlic on serum fibrinolytic activity in patients with coronary artery disease. Atherosclerosis 28: 155–159.
7. Bordia, A. and Verna S. A. (1980) Effect of garlic feeding on regression of experimental atherosclerosis in rabbits. Artery 7: 428–437.
8. Cavallito, C. J. and Bailey, J. H. (1944) Allicin, the antibacterial principle of Allium sativum. I. Isolation, physical properties and antibacterial action. J. Am. Chem. Soc. 66: 1944–1952; Cavallito, C. J., Buck, J. S. and Suter, C. M. (1944) ) Allicin, the antibacterial principle of Allium sativum. II. Determination of the chemical structure. J. Am. Chem. Soc. 66: 1952–1954.
9. Friedmann. T. E. and Haugen, G. E. (1943) J. Biol. Chem. 147: 415–442.
10. Han, J., Lawson, L., Han, G. and Han, P. (1995) A Spectrophotometric Method for Quantitative Determination of Allicin and Total Garlic Thiosulfinates. Anal Biochem. 225, 157–160.
11. Jansen, H., Muller, B., and Knobloch, K. (1987) Planta Medica 53: 559–562
12. Kennedy, J. F. and Cabral, J. M. S. (1983) "Immobilized Enzymes" in *Solid Phase Biochemistry*, Scouten, W. H., ed., John Wiley & Sons, New York.
13. Kieswetter, H., Jung, F., Morwietz, C., Pindur, G., Heiden, M. and. Wenzel, E. (1990) Effect of garlic on blood fluidity and fibrinolytic activity: A randomised placebo-controlled double-blind study. Brit. J. Clin. Pract. Suppl. 69: 24–29.
14. Knipschild, J. K. and Ter-Riet, G. (1989) Garlic, onions and cardiovascular risk factors. A review of the evidence from human experiments. Emphasis on commercially available preparations. Brit. J. Clin. Pharmacol. 28: 535–544.
15. Kohn, J. and Wilchek, M. (1982) Biochem. Biophys. Res. Commun. 107: 878
16. Lowry, O. H., Rosebrough, N. J. Farr, A. L. and Randall, R. J. (1951) J. Biol. Chem. 193: 265–275.
17. Makheja, A. N. and Bailey, J. N. (1990) Agents Actions 29: 360–363.
18. Mirelman, D., Monheit, D. J. and Varon, S. (1987) Inhibition of growth of enthamoeba histolitica by allicin, the active principle of garlic extract. J. Infect. Dis. 156: 243–244.
19. Miron, T. and Wilchek, M. (1982) Anal. Biochem. 126: 433–435.
20. Prabhune, A. and SivaRaman, H. (1990) Applied Biochem. and Biotech. 30:265–272.
21. Rabinkov A., Xiao-Zhu Z., Grafi G., Galili G. and Mirelman D. (1994) Alliin Lyase (Alliinase) from Garlic. J. Appl Biochem. Biotechnol. 48: 149–171.
22. Rabinkov A., Wilchek, M. and Mirelman D. (1995) Alliinase (alliin lyase) from garlic (*Allium sativum*) is glycosylated at ASN146 and forms a complex with a garlic mannose-specific lectin. Glycoconjugate J. 12: 690–698.
23. Stoll, A. and Seebeck, E. (1949) Helv. Chim. Acta 32: 197–205.
24. Stoll, A. and Seebeck, E. (1951) Chemical investigations of alliin, the specific principle of garlic. Adv. Enzymol. 11: 377–400.
25. Tramper, J. (1983) "Organic synthesis using immobilized enzymes", in *Solid Phase Biochemistry*, Scouten, W. H., ed., John Wiley & Sons, New York.
26. Wilchek, M. and Miron, T. (1982) Biochem Int. 4: 629–635.
27. Wilchek, M. and Miron, T. (1985) App. Biochem. Biotech. 11: 191–193.

What is claimed is:

1. Chemically immobilized garlic alliinase comprising garlic alliinase chemically immobilized by covalent binding to a carrier selected from the group consisting of organic natural and synthetic polymers and inorganic carriers.

2. Chemically immobilized alliinase in accordance with claim 1, wherein said carrier is an inorganic carrier selected from the group consisting of:
   (i) a controlled pore ceramic selected from the group consisting of titania, zirconia, and alumina;
   (ii) naturally occurring porous minerals selected from the group consisting of kieselguhr, attapulgite clays, pumice stone, and bentonite; and
   (iii) controlled pore glass (CPG).

3. Chemically immobilized alliinase in accordance with claim 1, wherein the carrier is an organic carrier which is a natural polymer selected from the group consisting of polysaccharides, proteins, and derivatives thereof; or a synthetic polymer selected from the group consisting of polystyrenes, polyacrylate- and poly methacrylate-type polymers, maleic anhydride-based polymers, polypeptides, vinyl and allyl polymers, and polyamides.

4. Chemically immobilized alliinase in accordance with claim 3, wherein the carrier is a polysaccharide selected from the group consisting of cellulose, starch, dextran, agar, agarose, chitin, chitosan, pectin, pectic acid, alginic acid and derivatives thereof.

5. Chemically immobilized alliinase in accordance with claim 3, wherein the carrier is a synthetic polymer which is (i) a polyacrylate polymer selected from the group consisting of polyacrylates, polymethacrylates, polymethacrylic acid anhydride, polyacrylamides, polyhydroxyalkyl methacrylates, polyglycidyl methacrylates, and polyacrylonitriles; (ii) a maleic anhydride-based polymer consisting of copolymers of maleic anhydride and ethylene; (iii) a polypeptide consisting of copolymers of L-leucine and 4-amino-DL-phenylalanine; (iv) a vinyl or allyl polymer selected from the group consisting of chemically-modified polyvinylaicohol, polyallylalcohol, and vinyl ether copolymers; or (v) a polyamide.

6. Chemically immobilized alliinase in accordance with claim 5, wherein the carrier is a polysaccharide or synthetic polymer and the alliinase is bound thereto via a spacer.

7. Chemically immobilized alliinase in accordance with claim 6, wherein the carrier is cellulose, agarose or a polymer of N-acryloyl-2-amino-2-hydroxymethyl-1,3-propanediol and the alliinase is bound thereto via an ε-aminocaproic acid spacer.

8. A column filled with a carrier selected from the group consisting of organic natural and synthetic polymers and inorganic carriers, wherein said carrier has garlic alliinase immobilized thereon by covalent binding.

9. A method for the continuous production of substantially pure allicin, comprising:
   forming a column filled with a carrier selected from the group consisting of organic natural and synthetic polymers and inorganic carriers, wherein said carrier has garlic alliinase immobilized thereon by covalent binding;
   adding a solution of alliin to the column; and
   collecting substantially pure allicin in the effluent.

10. A method in accordance with claim 9, wherein the carrier is an inorganic carrier selected from the group consisting of:

(i) a controlled pore ceramic selected from the group consisting of titania, zirconia, and alumina;

(ii) naturally occurring porous minerals selected from the group consisting of kieselguhr, attapulgite clays, pumice stone, and bentonite; and (iii) controlled pore glass (CPG).

11. A method in accordance with claim 9, wherein the carrier is an organic carrier which is a natural polymer selected from the group consisting of polysaccharides, proteins, and derivatives thereof; or a synthetic polymer selected from the group consisting of polystyrenes, polyacrylate- and poly methacrylate-type polymers, maleic anhydride-based polymers, polypeptides, vinyl and allyl polymers, and polyamides.

12. A method in accordance with claim 11, wherein the carrier is a polysaccharide selected from the group consisting of cellulose, starch, dextran, agar, agarose, chitin, chitosan, pectin, pectic acid, alginic acid and derivatives thereof.

13. A method in accordance with claim 11, wherein the carrier is a synthetic polymer which is (i) a polyacrylate polymer selected from the group consisting of polyacrylates, polymethacrylates, polymethacrylic acid anhydride, polyacrylamides, polyhydroxyalkyl methacrylates, polyglycidyl methacrylates, and polyacrylonitriles; (ii) a maleic anhydride-based polymer consisting of copolymers of maleic anhydride and ethylene; (iii) a polypeptide consisting of copolymers of L-leucine and 4-amino-DL-phenylalanine; (iv) a vinyl or allyl polymer selected from the group consisting of chemically-modified polyvinylalcohol, polyallylalcohol, and vinyl ether copolymers; or (v) a polyamide.

14. A method in accordance with claim 13, wherein the carrier is a polysaccharide or synthetic polymer and the alliinase is bound thereto via a spacer.

15. A method in accordance with claim 14, wherein the carrier is cellulose, agarose or a polymer of N-acryloyl-2-amino-2-hydroxymethyl-1,3-propanediol and the alliinase is bound thereto via an $\epsilon$-aminocaproic acid spacer.

* * * * *

UNITED STATES PATENT AND TRADEMARK OFFICE
CERTIFICATE OF CORRECTION

PATENT NO. : 6,689,588 B1
DATED : February 10, 2004
INVENTOR(S) : Erdei et al.

It is certified that error appears in the above-identified patent and that said Letters Patent is hereby corrected as shown below:

<u>Title page,</u>
Item [54], Title, delete "ALLICIAN" and insert -- ALLICIN --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,689,588 B1
DATED : February 10, 2004
INVENTOR(S) : Mirelman et al.

It is certified that error appears in the above-identified patent and that said Letters Patent is hereby corrected as shown below:

Title page,
Item [54], Title, delete "ALLICIAN" and insert therefor -- ALLICIN --.

Signed and Sealed this

Twenty-third Day of November, 2004

JON W. DUDAS
*Director of the United States Patent and Trademark Office*